United States Patent [19]

Sehgal et al.

[11] 4,375,463
[45] Mar. 1, 1983

[54] RAVIDOMYCIN AND PROCESS FOR PREPARATION

[75] Inventors: Surendra N. Sehgal, Dollard des Ormeaux; Claude Vezina, Oka, both of Canada

[73] Assignee: Ayerst, McKenna & Harrison, Inc., Montreal, Canada

[21] Appl. No.: 243,238

[22] Filed: Mar. 13, 1981

Related U.S. Application Data

[60] Continuation of Ser. No. 72,505, Sep. 4, 1979, abandoned, which is a division of Ser. No. 957,509, Nov. 3, 1978, Pat. No. 4,230,692.

[51] Int. Cl.$^3$ .............................................. A61K 35/00
[52] U.S. Cl. ..................................................... 424/122
[58] Field of Search ......................................... 424/122

*Primary Examiner*—Jerome D. Goldberg
*Attorney, Agent, or Firm*—Arthur E. Wilfond

[57] ABSTRACT

Ravidomycin is produced by culturing *Streptomyces ravidus* NRRL 11,300 in an aqueous nutrient medium. Ravidomycin is useful as an antibacterial and antitumor agent. Methods for its preparation and use are disclosed.

2 Claims, No Drawings

RAVIDOMYCIN AND PROCESS FOR PREPARATION

This is a continuation of now abandoned application Ser. No. 72,505, filed Sept. 4, 1979, which in turn is a division of application Ser. No. 957,509, filed Nov. 3, 1978, which became U.S. Pat. No. 4,230,692.

BACKGROUND OF THE INVENTION

This invention relates to a new composition of matter called ravidomycin, to a process for its preparation and pharmaceutical compositions therefor. Ravidomycin is useful as an antitumor agent against lymphocytic leukemia P-388, mammary tumors and colon 38.

SUMMARY OF THE INVENTION

Ravidomycin is a chemical compound producible by culturing a ravidomycin-producing organism in an aqueous nutrient medium. Ravidomycin exhibits antitumor activity. The ravidomycin producing organism and ravidomycin are described in detail in the aforementioned ancestor application 957,509, the pertinent portions of which are incorporated herein by the reference.

Also, ravidomycin is useful for treating tumors in a mammal when administered to said mammal in an antitumor effective amount.

A convenient form for administering ravidomycin involves a pharmaceutical composition of ravidomycin and a pharmaceutically acceptable carrier.

DETAILED DESCRIPTION

Ravidomycin reduces tumor size in and prolongs the survival time of tumor-bearing mammals. The effectiveness of ravidomycin in this respect can be demonstrated in the laboratory with rodents having transplanted tumors. Details of methods used to evaluate this effect are described in various publications; for example, R. I. Geran et al., Cancer Chemother. Rep., Part 3, 3, 1–103(1972) and references therein.

Tables 4, 5 and 6 show the effects of therapy with ravidomycin on lymphatic leukemia, colon tumors and mammary tumors in rodents.

More specifically, Table 1 shows the prolongation of survival time of female $CDF_1$ mice implanted with lymphatic leukemia P338 by administering Ravidomycin; Table 5 shows the reduction in size of colon 38 tumors in female $BDF_1$ mice by administering Ravidomycin; and Table 6 shows the reduction in size of $CD8F_1$ mammary tumors in female $CD8F_1$ rats by administering Ravidomycin.

TABLE 1

Effect of Ravidomycin on Survival Time of Mice Implanted with Lymphatic Leukemia P-388 (ascetic).

| Dose/Inj mg/kg | Ave. Wt. Difference of Animals (T − C., g) | Survivors on Day 5 | MST days T | MST days C | T/C% MST |
|---|---|---|---|---|---|
| 400 | −3.4 | 6/6 | 7.9 | 12.7 | — |
| 200 | −4.6 | 5/6 | 11.0 | 12.7 | 86 |
| 100 | −1.0 | 6/6 | 19.0 | 12.7 | 149 |
| 100 | −1.2 | 6/6 | 25.0 | 10.5 | 238 |
| 50 | −1.4 | 6/6 | 14.3 | 10.5 | 136 |
| 25 | −0.3 | 5/6 | 12.0 | 10.5 | 114 |

Treatment:
Single intraperitoneal injection on days 1, 5 and 9 in a vehicle of hydroxypropylcellulose.
Evaluation:
T/C% = Median Survival Time (MST) in days of treated animals (T) control animals (C) × 100. A T/C% of 125 or greater is considered as a significant prolongation of host survival. Evaluation done on day 30.

TABLE 2

Effect of Ravidomycin on Colon 38 Tumor Weight in Mice

| Dose/Inj. mg/kg | Ave. Net Wt. Difference of Animals (T − C., g) | Survivors Day 5 | MTW mg T | MTW mg C | T/C% MTW |
|---|---|---|---|---|---|
| 400 | 3.4 | 10/10 | 0 | 1273 | 0 |
| 200 | .4 | 10/10 | 175 | 1273 | 13 |
| 100 | 3.2 | 10/10 | 384 | 1273 | 30 |
| 50 | 3.8 | 10/10 | 1080 | 1273 | 84 |
| 25 | 7.2 | 10/10 | 661 | 1273 | 51 |
| 12.5 | 6.2 | 10/10 | 668 | 1273 | 52 |

Treatment:
Single intraperitoneal injection on days 2, 9 and 16 in a vehicle of hydroxypropylcellulose.
Evaluation:
T/C% = Median tumor weight (MTW) estimated from tumor diameter of treated animals (T)/control animals (C) × 100. A T/C% of 42 or less is considered as a significant inhibitor of tumor growth. Evaluation done on day 20.

TABLE 3

Effect of Ravidomycin on $CD8F_1$ Mammary Tumors in Rats

| Dose/Inj. mg/kg | Ave. Net Wt. Difference of Animals (T − C., g) | Survivors Day 5 | MTW mg T | MTW mg C | T/C% MTW |
|---|---|---|---|---|---|
| 400 | −4.8 | 0/10 | 0 | 1116 | — |
| 200 | −7.6 | 5/10 | 0 | 1116 | — |
| 100 | −7.4 | 10/10 | 1 | 1116 | 0 |
| 50 | −3.8 | 10/10 | 1 | 1116 | 0 |
| 25 | −2.4 | 9/10 | 576 | 1116 | 51 |
| 12.5 | −.5 | 9/10 | 864 | 1116 | 77 |

Treatment:
Single intraperitoneal injection on days 1, 8, 15, 22 and 29 in vehicle of hydroxypropylcellulose.
Evaluation:
T/C% = Median tumor weight (MTW) estimated from tumor diameter of treated animals (T)/control animals (C) × 100. A T/C% of 42 or less is considered as a significant inhibitor of tumor growth. Evaluation done on day 30.

When ravidomycin of this invention is employed as an antitumor agent in warm-blooded animals, e.g. rats, it may be used alone or in combination with pharmaceutically acceptable carriers, the proportion of which is determined by the solubility and chemical nature of the compound, chosen route of administration and standard biological practice. For example, an antitumor effective amount of ravidomycin can be administered orally in solid form containing such excipients as starch, sugar, certain types of clay and so forth. Similarly, such an amount can also be administered orally in the form of solutions or suspensions, or injected parenterally. For parenteral administration ravidomycin can be used in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The dosage of ravidomycin will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compound of this invention is most desirably administered at a concentration level that will generally afford antitumor effective results without causing any harmful or deleterious side effects.

When used as an antitumor agent, ravidomycin is administered at a dose about 5 to 250 mg per kilogram of body weight per day, although the aforementioned variations will occur. However, a dosage level that is in the range from about 50 to about 100 mg per kilogram of body weight per day is most desirably employed in order to achieve effective results. The acute interperitoneal $LD_{50}$ in mice is greater than 400 mg/kg of body weight.

Ravidomycin also can be used to produce beneficial effects in the treatment of malignant tumors when combined with a therapeutically effective amount of an antineoplastic agent commonly used in cancer therapy. Such antineoplastic agents include the alkylating agents, for example, busulfan, chlorambucil, cyclophosphamide, mechlorethamine hydrochloride, melphalan, pipobroman, thiotepa and uracil mustard; antimetabolites, for example, cytarabine, fluorouracil, floxuridine, mercaptopurine, methotrexate and thioguanine; miscellaneous anticancer agents, for example, dacarbazine, hydroxyurea, mitotane, procarbazine hydrochloride, quinacrine hydrochloride, vinblastine sulfate and vincristine sulfate; estrogens, for example, chlorotrianisene, conjugate estrogens (e.g. PREMARIN ®), diethylstilbestrol and the like; androgens, for example, methyltestosterone, testosterone and the like; adrenal corticosteriods, for example, prednisone and the like; progestagens, for example, megestrol, hydroxyprogesterone caproate and the like; radioactive isotopes; and antibiotics, for example, bleomycin sulfate, doxorubicin hydrochloride and the like. Suitable methods of administration, compositions and dosages of the antineoplastic agents are described in medical textbooks; for instance, "PHYSICIANS' DESK REFERENCE", 32nd ed., Medical Economics Co., Oradell, N.J. U.S.A., 1978 and "AMA DRUG EVALUATIONS", 3 ed. PSG Publishing Company, Inc., Littleton, Mass., U.S.A., pp 1106–1151, 1977. When used in combination, ravidomycin is administered as described previously; however, a lower dose can be used for efficacious results. For example, a suitable dose range of ravidomycin, when used in combination with an antineoplastic agent, is from about 1.0 to 100 mg per kilogram of body weight per day.

We claim:

1. A method of treating transplanted tumors, selected from the group consisting of lymphocytic leukemia P-388, colon 38, and $CD8F_1$ mammary tumor, in a mammal, which comprises administering to said mammal an antitumor effective amount of ravidomycin.

2. A method of treating transplantable tumors, selected from the group consisting of lymphocytic leukemia, colon and mammary tumor, in a tumor bearing mammal, which comprises administering to said mammal an antitumor effective amount of ravidomycin.

* * * * *